United States Patent
Devane et al.

(10) Patent No.: US 6,228,398 B1
(45) Date of Patent: May 8, 2001

(54) MULTIPARTICULATE MODIFIED RELEASE COMPOSITION

(75) Inventors: John G. Devane; Paul Stark; Niall M. M. Fanning, all of Athlone (IE)

(73) Assignee: Elan Corporation, PLC, Dublin (IE)

(*) Notice: Subject to any disclaimer, the term of this patent is extended or adjusted under 35 U.S.C. 154(b) by 0 days.

(21) Appl. No.: 09/566,636

(22) Filed: May 8, 2000

Related U.S. Application Data

(63) Continuation of application No. PCT/US99/25632, filed on Nov. 1, 1999.
(60) Provisional application No. 60/106,726, filed on Nov. 2, 1998.

(51) Int. Cl.$^7$ .................................................. A61K 9/14
(52) U.S. Cl. .................... 424/484; 424/464; 424/465; 424/468; 424/469; 424/456; 424/451; 424/472
(58) Field of Search .................... 424/458, 497, 424/462, 472, 464, 468, 484, 465, 469, 456, 451

(56) References Cited

U.S. PATENT DOCUMENTS

| | | | |
|---|---|---|---|
| 4,728,512 | 3/1988 | Mehta et al. | 424/458 |
| 4,794,001 | 12/1988 | Mehta et al. | 424/458 |
| 4,888,178 | 12/1989 | Rotini et al. | 424/468 |
| 4,904,476 | 2/1990 | Mehta et al. | 424/456 |
| 5,158,177 | 10/1992 | Abramowitz et al. | 424/458 |
| 5,445,829 | * 8/1995 | Paradissis et al. | 424/480 |
| 5,639,476 | * 6/1997 | Oshlack et al. | |
| 5,726,316 | * 3/1998 | Crooks et al. | |
| 5,837,284 | 11/1998 | Mehta et al. | 424/459 |

FOREIGN PATENT DOCUMENTS

| | | |
|---|---|---|
| 0 274 734 A1 | * 7/1988 | (EP) . |
| 0 274 734 | 7/1988 | (EP) . |
| WO9703672 | 2/1997 | (WO) . |
| WO98/14168 | 4/1998 | (WO) . |

OTHER PUBLICATIONS

Shah, et al., *J. Cont. Rel.* (1989) 9:169–175.
Giumchedi, et al., *Int. J. Pharm* (1991) 77:177–181.
Conte, et al. *Drug. Del. Ind. Pharm.* (1989) 15:2583–2596.

* cited by examiner

Primary Examiner—Thurman K. Page
Assistant Examiner—Rachel Bennett
(74) Attorney, Agent, or Firm—Kilpatrick Stockton LLP

(57) ABSTRACT

The invention relates to a multiparticulate modified release composition that in operation delivers an active ingredient in a pulsed or bimodal manner. The multiparticulate modified release composition comprises an immediate release component and a modified release component; the immediate release component comprising a first population of active ingredient containing particles and the modified release component compnsimg a second population of active ingredient containing particles coated with a controlled release coating; wherein the combination of the immediate release and modified release components in operation deliver the active ingredient in a pulsed or a bimodal manner. The invention also relates to a solid oral dosage form containing such a multiparticulate modified release composition. The plasma profile achieved by the multiparticulate modified release composition is advantageous in reducing patient tolerance to the active ingredient and in increasing patient compliance by reducing dosage frequency.

37 Claims, 1 Drawing Sheet

MULTIPARTICULATE MODIFIED RELEASE COMPOSITION

This application is a continuation of PCT/US99/25632, filed Nov. 1, 1999, which claims benefit of Ser. No. 60/106726, filed Nov. 2, 1998.

FIELD OF THE INVENTION

The present invention relates to a multiparticulate modified release composition. In particular the present invention relates to a multiparticulate modified release composition that in operation delivers an active ingredient in a pulsatile manner. The present invention further relates to solid oral dosage forms containing such a multiparticulate controlled release composition.

DESCRIPTION OF THE PRIOR ART

The plasma profile associated with the administration of a drug compound may be described as a "pulsatile profile" in which pulses of high active ingredient concentration, interspersed with low concentration troughs, are observed. A pulsatile profile containing two peaks may be described as "bimodal". Similarly, a composition or a dosage form which produces such a profile upon administration may be said to exhibit "pulsed release" of the active ingredient.

Conventional frequent dosage regimes in which an immediate release (IR) dosage form is administered at periodic intervals typically gives rise to a pulsatile plasma profile. In this case, a peak in the plasma drug concentration is observed after administration of each IR dose with troughs (regions of low drug concentration) developing between consecutive administration time points. Such dosage regimes (and their resultant pulsatile plasma profiles) have particular pharmacological and therapeutic effects associated with them. For example, the wash out period provided by the fall off of the plasma concentration of the active ingredient between peaks has been thought to be a contributing factor in reducing or preventing patient tolerance to various types of drugs.

Many controlled release drug formulations are aimed at producing a zero-order release of the drug compound. Indeed, it is often a specific object of these formulations to minimise the peak-to-trough variation in drug plasma levels associated with conventional frequent dosage regimes. However, some of the therapeutic and pharmacological effects intrinsic in a pulsatile system may be lost or diminished as a result of the constant or nearly constant plasma levels achieved by zero-order release drug delivery systems. Thus, a modified release composition or formulation which substantially mimics the release of frequent IR dosage regimes, while reducing the need for frequent dosing, is desirable.

A typical example of a drug which may produce tolerance in patients is rnethylphenidate. Methylphenidate, or α-phenyl-2-piperidine acetic acid methyl ester, is a stimulant affecting the central nervous and respiratory systems and is primarily used in the treatment of attention deficit disorder. After absorption from the gastrointestinal tract (GIT), drug effects persist for 3–6 hours after oral administration of conventional IR tablets or up to about 8 hours after oral administration of extended release formulations. The total dosage is typically in the range of 5–30 mg per day, in exceptional cases rising to 60 mg/day. Under conventional dosage regimes, methylphenidate is given twice daily, typically with one dose given before breakfast and a second dose given before lunch. The last daily dose is preferably given several hours before retiring. Adverse effects associated with methylphenidate treatment include insonmia and the development of patient tolerance.

WO 98/14168 (Alza Corp.) teaches a dosage form and a method of administering methylphenidate in a sustained and constantly ascending rate. The dosage form disclosed comprises a plurality of beads comprising a hydrogel matrix with increasing amounts of the active ingredient therein, coated with varying amounts of a release rate controlling material. Appropriate combinations of the active ingredient dose and the number and thickness coating layers can be selected to give an ascending release profile in which the plasma concentration of the active ingredient continually increases over a give n period of tine. In contrast to the present invention, an object of WO 98/14168 is to provide a dosage form to specifically avoid uneven blood levels (characterised by peaks and troughs) associated with conventional treatments using immediate release dosage formulations.

WO 97/03672 (Chiroscience Ltd.) discloses that methyiphenidate exhibits a therapeutic effect when administered in the form of a racemic mixture or in the form of a single isomer (such as the RR d-threo enantiomer). Further, WO 97/03763 (Chiroscience Ltd.) discloses a sustained release formulation containing dtmp. This disclosure teaches the use of a composition comprising a coating through which the dtmp passes in order to atttain sustained release and achieve serum levels (of the active,ingredient) of at least 50% $c_{max}$ over a period of at least 8 hours. Thus, this formulation does not deliver the active ingredient in a pulsatile manner.

Shah et al., *J Cont. Rel.* (1989) 9:169–175 discloses that certain types of hydroxypropyl methylcellulose ethers compressed into a solid dosage form with a therapeutic agent may give a bimodal release profile. However, it was noted that while polymers from one supplier yielded a bimodal profile, the same polymers with almost identical product specifications obtained from a different source gave non-bimodal release profiles.

Giunchedi et al., *Int. J. Pharm* (1991) 77:177–181 discloses the use of a hydrophilic matrix multiple-unit formulation for the pulsed release of ketoprofen. Giunchedi et al. teach that ketoprofen is rapidly eliminated from the blood after dosing (plasma half-life 1–3 hours) and consecutive pulses of drug may be more beneficial than constant release for some treatments. The multiple-unit formulation disclosed comprises four identical hydrophilic matrix tablets placed in a gelatin capsule. Although the in vivo studies show two peaks in the plasma profile there is no well defined wash out period and the variation between the peak and trough plasma levels is small.

Conte et al., *Drug Dev. Ind. Pharm,* (1989) 15:2583–2596 and EP 0 274 734 (Pharmidea Srl) teach the use of a three layer tablet for delivery of ibuprofen in consecutive pulses. The three layer tablet is made up of a first layer containing the active ingredient, a barrier layer (the second layer) of semi-permeable material which is interposed between the first layer and a third layer containing an additional amount of active ingredient. The barrier layer and the third layer are housed in an impermeable casing. The first layer dissolves upon contact with a dissolving fluid while the third layer is only available after dissolution or rupture of the barrier layer. In such a tablet the first portion of active ingredient must be released instantly. This approach also requires the provision of a semi-permeable layer between the first and third layers in order to control the relative rates of delivery of the two portions of active ingredient. Additionally, rupture of the semi-permeable layer leads to uncontrolled dumping of the second portion of the active ingredient which may not be desirable.

U.S. Pat. No. 5,158,777 (E. R. Squibb & Sons Inc.) discloses a formulation comprising captopril within an enteric or delayed release coated pH stable core combined with additional captopril which is available for immediate release following administration. In order to form the pH stable core, chelating agents such as disodium edetate or surfactants such as polysorbate 80 are used either alone or in combination with a buffering agent. The compositions have an amount of captopril available for immediate release following oral administration and an additional amnount of pH stabilised captopril available for release in the colon.

U.S. Pat. Nos. 4,728,512, 4,794,001 and 4,904,476 (American Home Products Corp.) relate to preparations providing three distinct releases. The preparation contains three groups of spheroids containing an active medicinal substance: the first group of spheroids is uncoated and rapidly disintegrates upon ingestion to release an initial dose of medicinal substance; the second group of spheroids is coated with a pH sensitive coat to provide a second dose; and the third group of spheroids is coated with a pH independent coat to provide to third dose. The preparation is designed to provide repeated release of medicinal substances which are extensively metabolised presystemically or have relatively short elimination half-lives.

U.S. Pat. No. 5,837,284 (Mehta et al) discloses a methylphenidate dosage form having immediate release and delayed release particles. The delayed release is provided by the use of armmonio methacrylate pH independent polymers combined with certa fillers.

Accordingly, it is an object of the present invention to provice a multiparticulate modified release composition containing an active ingredient which in operation produces a plasma profile substantially similar to the plasma profile produced by the administration of two or more IR dosage forms given sequentially.

It is a further object of the invention to provide a multi-particulate modified release composition which in operation delivers an active ingredient in a pulsatile manner.

Another object of the invention is to provide a multiparticulate modified release composition which substantially mimics the pharmacological and therapeutic effects produced by the administration of two or more IR dosage forms given sequentially.

Another object of the present invention is to provide a multiparticulate modified release composition which substantially reduces or eliminates the development of patient tolerance to the active ingredient of the composition.

Another object of the invention is to provide a multiparticulate modified release composition in which a first portion of the active ingredient is released immediately upon administration and a second portion of the active ingredient is released rapidly after an initial delay period in a bimodal manner.

Another object of the invention is to provide a multiparticulate modified release composition capable of releasing the active ingredient in a bimodal or multi-modal manner in which a first portion of the active ingredient is released either immediately or after a delay time to provide a pulse of drug release and one or more additional portions of the active ingredient are released each after a respective lag time to provide additional pulses of drug release.

Another object of the invention is to provide solid oral dosage forms comprising a multiparticulate modified release composition of the present invention.

Other objects of the invention include provision of a once daily dosage form of methylphenidate which, in operation, produces a plasma profile substantially similar to the plasma profile produced by the administration of two immediate release dosage forms given sequentially and a method for treatment of attention deficit disorder based on administration of such a dosage form.

BRIEF DESCRIPTION OF THE INVENTION

The above objects are realised by a multiparticulate modified release composition having a first component comprising a first population of active ingredient-containing particles and a second component comprising a second population of active ingredient-containing particles. The active ingredient contained in the first and second components can be the same or different and active ingredient-containing particles of the second component are coated with a modified release coating. Alternatively or additionally, the second population of active ingredient containing particles further comprises a modified release matrix material. Following oral delivery, the composition in operation delivers the active ingredient or active ingredients in a pulsatile manner.

In a preferred embodiment of a multiparticulate modified release composition according to the invention the first component is an immediate release component.

The modified release coating applied to the second population of active ingredient containing particles causes a lag time between the release of active ingredient from the first population of active ingredient contaning particles and the release of active ingredient from the second population of active ingredient containing particles. Similarly, the presence of a modified release matrix material in the second population of active ingredient containing particles causes a lag time between the release of active ingredient from the first population of active ingredient containing particles and the release of active ingredient from the second population of active ingredient containing particles. The duration of the lag time may be varied by altering the composition and/or the amount of the modified release coating and/or altering the composition and/or amount of modified release matrix material utilised. Thus, the duration of the lag time can be designed to mimic a desired plasma profile.

Because the plasma profile produced by the multiparticulate modified release composition upon administration is substantially similar to the plasma profile produced by the administration of two or more IR dosage forms given sequentially, the multiparticulate controlled release composition of the present invention is particularly useful for administering active ingredients for which patient tolerance may be problematical. This multiparticulate modified release composition is therefore advantageous for reducing or mimimising the development of patient tolerance to the active ingredient in the composition.

In a preferred embodiment of the present invention, the active ingredient is methylphenidate and the composition in operation delivers the active ingredient in a bimodal or pulsed manner. Such a composition in operation produces a plasma profile which substantially mimics that obtained by the sequential administration of two IR doses as, for instance, in a typical methylphenidate treatment regime.

The present invention also provides solid oral dosage forms comprising a composition according to the invention.

The present invention further provides a method of treating an animal, particularly a human in need of treatment utilising the active ingredient, comprising administering a therapeutically effective amount of a composition or solid oral dosage form according to the invention to provide pulsed or bimodal administration of the active ingredient.

Advantages of the present invention include reducing the dosing frequency required by conventional multiple IR dosage regimes while still maintaining the benefits derived from a pulsatile plasma profile. This reduced dosing frequency is particularly advantageous in the case of children in taat it eliminates the need for dosing during the middle of the school day which can be both disruptive and embarrassing for the patient. It is also advantageous in terms of patient compliance to have a formulation which may be administered at reduced frequency. The reduction in dosage frequency made possible by utilising the present invention would contribute to reducing health care costs by reducing the amount of time spent by health care workers on the administration of drugs. In the case of methylphenidate, and other controlled substances, the use of a once-daily formulation (in place of multiple IR doses) reduces or eliminates the need for the storage of controlled substances on the premises of schools or other institutions.

DETAILED DESCRIPTION OF THE INVENTION

Figure 1:
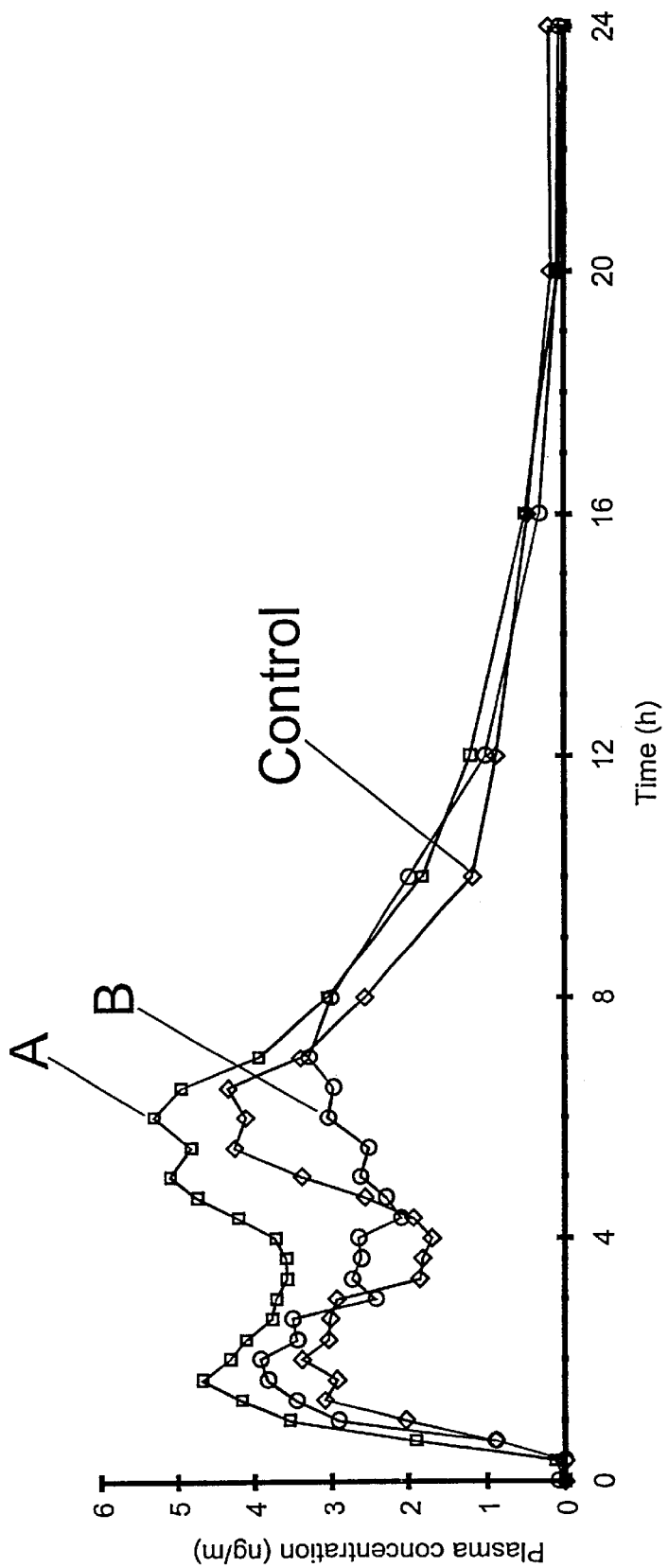
FIG. 1 shows methylphenidate plasma profiles following oral administration of the following three formulations to human volunteers: A—20 mg methylphenidate formulation having an immediate release component comprising particles containing a total of 10 mg methylphenidate (according to Table 1 (ii)) and a modified release component comprising particles containing a total of 10 mg methylphenidate (according to Table 2 (viii); IR particles coated to a 30% weight gain);B—20 mg methylphenidate formulation having an immediate release component comprising particles containing a total 10 mg methylphenidate (according to Table 1 (ii)) and a modified release component comprising particles containing a total of 10 mg methylphenidate (according to Table 2 (vii); IR particles coated to a 30% weight gain); and Control—two doses of 10 mg Ritalin® Hydrochloride (IR) tablets administered at times 0 and 4 hours (total of 20 mg methylphenidate administered).

The term "particulate" as used herein refers to a state, of matter which is characterised by the presence of discrete particles, pellets, beads or granules irrespective of their size, shape or morphology. The term "multiparticulate" as used herein means a plurality of discrete, or aggregated, particles, pellets, beads, granules or mixture thereof irrespective of their size, shape or morphology.

The term "modified release" as used herein in relation to the composition according to the invention or a coating or coating material or used in any other context means release which is not immediate release and is taken to encompass controlled release, sustained release and delayed release.

The term "time delay" as used herein refers to the duration of time between administration of the composition and the release of the active ingredient from a particular component.

The term "lag time" as used herein refers to the time between delivery of active ingredient from one component and the subsequent delivery of active ingredient from another component.

The invention will be described in detail with respect to methylphenidate as a specific example of an active ingredient particularly suited to formulation in a multiparticulate modified release composition according to the present invention.

The multiparticulate modified release composition of the invention may have more than two active ingredient-containing components. In this case the release of active ingredient from the second and subsequent components is modified such that there is a lag time between the release of active ingredient from the first component and each subsequent component. The number of pulses in the profile arising from such a composition in operation will depend on the number of active ingredient containing components in the composition. A composition containing three active ingredient-containing components will give rise to three pulses in the profile.

Any active ingredient for which it is useful to combine the advantages of a pulsatile plasma profile with a reduced frequency dosage regime may be used in practice of the present invention. Particularly usefull in the practice of the invention include active ingredients whose pharmacological and/or therapeutic effects benefit from having a wash-out period between plasma concentration peaks, such as those active ingredients susceptible to the development of patient tolerance. Example active ingredients include but are not limited to peptides or proteins, hormones, analgesics, anti-migraine agents, anti-coagulant agents, narcotic antagonists, chelating agents, anti-anginal agents, chemotherapy agents, sedatives, anti-neoplastics, prostaglandins and antidiuretic agents, drug compounds acting on the central nervous system such as cerebral stimulants, for example methylphenidate; pain management active ingredients; alkaloids such as opiates, for example morphine; cardiovascular drugs, such as nitrates; and agents for treating rheumatic conditions. It is further appreciated that the present invention may be used to deliver a number of drugs including, but not limited to, peptides, proteins or hormones such as insulin, calcitonin, calcitonin gene regulating protein, atrial natriuretic protein, colony stimulating factor, betaseron, erythropoietin (EPO), interferons such as $\alpha$, $\beta$ or $\gamma$ interferon, somatropin, somatotropin, somastostatin, insulin-like growth factor (somatomedins), luteinizing hoimone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof.

The active ingredient in each component may be the same or different For example, a composition in which the first component contains a first active ingredient and the second component comprises a second active ingredient may be desirable for combination therapies. Indeed, two or more active ingredients may be incorporated into the same component when the active ingredients are compatible with each other. A drug compound present in one component of the composition may be accompanied by, for example, an enhancer compound or a sensitiser compound in another component of the composition, in order to modify the bioavailability or therapeutic effect of the drug compound.

As used herein, the term "enhancer" refers to a compound which is capable of enhancing the absorption and/or bioavailability of an active ingredient by promoting net transport across the GIT in an animal, such as a human. Enhancers include but are not limited to medium chain fatty acids; salts, esters, ethers and derivatives thereof, including glycerides and triglycerides; non-ionic surfactants such as those that can be prepared by reacting ethylene oxide with a fatty acid, a fatty alcohol, an alkylphenol or a sorbitan or glycerol fatty acid ester; cytochrome P450 inhibitors, P-glycoprotein inhibitors and the like; and mixtures of two or more of these agents.

The proportion of active ingredient contained in each component may be the same or different depending on the desired dosing regime. The active ingredient may be present, in the first component individually or in combination with the active ingredient (or active ingredients) in the second component, in any amount sufficient to elicit a therapeutic response. The active ingredient (or active ingredients), when applicable, may be present either in the form of one substantially optically pure enantiomer or as a mixture, racemic or otherwise, of enantiomers. The active ingredient is preferably present in a composition in an amount of from 0.1–500 mg, preferably in the amount of from 1–100 mg. When the active ingredient is methylphenidate, it is preferably present in the first component in an amount of from 0.5–60 mg; more preferably the active ingredient is present in the frrst component in an amount of from 2.5–30 mg. The active ingredient is present in the subsequent components in an amount within a similar range to that described for the first component.

The time release characteristics for the release of the active ingredient from each of the components may be varied by modifying the composition of each component, including modifying any of the excipients or coatings which may be present. In particular the release of the active may be controlled by changing the composition and/or the amount of the modified release coating on the particles, if such a coating is present. If more than one modified release component is present, the modified release coating for each of these components may be the same or different. Similarly, when modified release is facilitated by the inclusion of a modified release matrix material, release of the active ingredient may be controlled by the choice and amount of modified release matrix material utilised. The modified release coating may be present, in each component, in any amount that is sufficient to yield the desired delay time for each particular component. The modified release coating may be preset, in each component, in any amount that is sufficient to yield the desired time lag between components.

The lag time or delay time for the release of the active ingredient from each component may also be varied by modifying the composition of each of the components, including modifying any excipients and coatings which may be present. For example the first component may be an immediate release component wherein the active ingredient is released substantially immediately upon administration. Alternatively, the first component may be, for example, a time-delayed immediate release component in which the active ingredient is released substantially immediately after a time delay. The second component may be, for example, a time-delayed immediate release component as just described or, alternatively, a time-delayed sustained release or extended release component in which the active ingredient is released in a controlled fashion over an extended period of time.

As will be appreciated by those skilled in the art, the exact nature of the plasma concentration curve will be influenced by the combination of all of these factors just described. In particular, the lag time between the delivery (and thus also the on-set of action) of the active ingredient in each component may be controlled by varying the composition and coating (if present) of each of the components. Thus by variation of the composition of each component (including the amount and nature of the active ingredient(s)) and by variation of the lag time, numerous release and plasma profiles may be obtained. Depending on the duration of the lag time between the release of active ingredient from each component and the nature of the release from each component (i.e. immediate release, sustained release etc.), the pulses in the plasma profile may be well separated and clearly defined peaks (e.g. when the lag time is long) or the pulses may be superimposed to a degree (e.g. in when the lag time is short).

In a preferred embodiment, the multiparticulate modified release composition according to the present invention has an immediate release component and at least one modified release component, the immediate release component comprising a first population of active ingredient containing particles and the modified release components comprising second and subsequent populations of active ingredient containing particles. The second and subsequent modified release components may comprise a controlled release coating. Additionally or alternatively, the second and subsequent modified release components may comprise a modified release matrix material. In operation, administration of such a multiparticulate modified release composition having, for example, a single modified release component results in characteristic pulsatile plasma concentration levels of the active ingredient in which the immediate release component of the composition gives rise to a first peak in the plasma profile and the modified release component gives rise to a second peak in the plasma profile. Embodiments of the invention comprising more than one modified release component give rise to further peaks in the plasma profile.

Such a plasma profile produced from the administration of a single dosage unit is advantageous when it is desirable to deliver two (or more) pulses of active ingredient without the need for administration of two (or more) dosage units. Additionally, in the case of some disorders it is particularly useful to have such a bimodal plasma profile. For example, a typical methylphenidate treatment regime consists of administration of two doses of an immediate release dosage formulation given four hours apart. This type of regime has been found to be therapeutically effective and is widely used. The plasma profile produced by such an administration regime is illustrated by the "Control" curve in FIG. 1. As previously mentioned, the development of patient tolerance is an adverse effect sometimes associated with methylphenidate treatments. It is believed that the trough in the plasma profile between the two peak plasma concentrations is advantageous in reducing the development of patient tolerance by providing a period of wash out of the active ingredient. Drug delivery systems which provide zero order or pseudo zero order delivery of the active ingredient do not facilitate this wash out process.

Any coating material which modifies the release of the active ingredient in the desired manner may be used. In particular, coating materials suitable for use in the practice of the invention include but are not limited to polymer coating materials, such as cellulose acetate phthalate, cellulose acetate trimaletate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the Trade Mark Eudragit® S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers in which the degree of crosslining is low so as to facilitate adsorption of water and expansion of the polymer matrix, hydoxypropyl cellulose, hydroxypropyl methylcellulose, polyvinylpyrrolidone, crosslinked starch, microcrystalline cellulose, chitin, arninoacryl-methacrylate copolymer (Eudragit® RS-PM, Rohm & Haas), pullulan, collagen, casein, agar, gum arabic, sodium carboxymethyl cellulose, (swellable hydrophilic polymers) poly (hydroxyalkyl methacrylate) (m. wt. ~5k–5,000k), polyvinylpyrrolidone (m. wt. ~10k–360k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. ~30k–300k), polysaccharides such as agar, acacia, karaya, tragacanth, algins and guar, polyacrylamides, Polyox® polyethylene oxides (m. wt. ~100k–5,000k), AquaKeep® acrylate polymers, diesters of polyglucan, crosslinked polyvinyl alcohol and poly N-vinyl-2-pyrrolidone, sodium starch glucolate (e.g. Explotab®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyoxe®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

When the modified release component comprises a modified release matrix material, any suitable modified release matrix material or suitable combination of modified release matrix materials may be used. Such materials are known to those skilled in the art. The term "modified release matrix material" as used herein includes hydrophilic polymers, hydrophobic polymers and mixtures thereof which are capable of modifying the release of an active ingredient dispersed therein in vitro or in vivo. Modified release matrix materials suitable for the practice of the present invention include but are not limited to microcrytalline cellulose, sodium carboxymethylcellulose, hydoxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose acteate, cellulose acetate butyrate, cellulose acteate phthalate, cellulose acteate trimellitate, polyvinylacetate phthalate, polyalkylmethacrylates, polyvinyl acetate and mixture thereof.

A multiparticulate modified release composition according to the present invention may be incorporated into any suitable dosage form which facilitates release of the active ingredient in a pulsatile manner. Typically, the dosage form may be a blend of the different populations of active ingredient containing particles which make up the immediate release and the modified release components, the blend being filled into suitable capsules, such as hard or soft gelatin capsules. Alternatively, the different individual populations of active ingredient containing particles may be compressed (optionally with additional excipients) into mini-tablets which may be subsequently filled into capsules in the appropriate proportions. Another suitable dosage form is that of a multilayer tablet. In this instance the first component of the multiparticulate modified release composition may be compressed into one layer, with the second component being subsequently added as a second layer of the multilayer tablet. The populations of active ingredient containing particles making up the composition of the invention may flrher be included in rapidly dissolving dosage forms such as an effervescent dosage form or a fast-melt dosage form.

The composition according to the invention comprises at least two populations of active ingredient containing particles which have different in vitro dissolution profiles.

Preferably, in operation the composition of the invention and the solid oral dosage forms containing the composition release the active ingredient such that substantially all of the active ingredient contained in the first component is released prior to release of the active ingredient from the second component. When the first component comprises an IR component, for example, it is preferable that release of the active ingredient from the second component is delayed until substantially all the active ingredient in the IR component has been released. Release of the active ingredient from the second component may be delayed as detailed above by the use of a modified release coating and/or a modified release matrix material.

More preferably, when it is desirable to minimise patient tolerance by providing a dosage regime which facilitates wash-out of a first dose of active ingredient from a patient's system, release of the active ingredient from the second component is delayed until substantially all of the active ingredient contained in the first component has been released, and further delayed until at least a portion of the active ingredient released from the first component has been cleared from the patient's system. In a preferred embodiment, release of the active ingredient from the second component of the composition in operation is substantially, if not completely, delayed for a period of at least about two hours after administration of the composition.

When the active ingredient is methylphenidate, release of the active ingredient from the second component of the composition in operation is substantially, if not completely, delayed for a period of at least about four hours, preferably about four hours, after administration of the composition.

In the following Examples all percentages are weight by weight unless otherwise stated. The term "purified water" as used throughout the Examples refers to water that has been purified by passing it through a water filtration system.

EXAMPLE 1

Multiparticulate Modified Release Composition Containing Methylphenidate

A multiparticulate modified release composition according to the present invention comprising an immediate release component and a modified release component and containing methylphenidate as the active ingredient is prepared as follows.

(a) Immediate release component.

A solution of methylphenidate HCl (50:50 racemic mixture) is prepared according to any of the formulations given in Table 1. The methylphenidate solution is then coated onto nonpareil seeds to a level of approximately 16.9% solids weight gain using, for example, a Glatt GPCG3 (Glatt, Protech Ltd., Leicester, UK) fluid bed coating apparatus to form the IR particles of the imniediate release component

TABLE 1

Immediate release component solutions

| | Amount, % (w/w) | |
|---|---|---|
| Ingredient | (i) | (ii) |
| Methylphenidate HCl | 13.0 | 13.0 |
| Polyethylene Glycol 6000 | 0.5 | 0.5 |
| Polyvinylpyrrolidone | 3.5 | |
| Purified Water | 83.5 | 86.5 |

(b) Modifted release component.

Methylphenidate containing delayed release particles are prepared by coating immediate release particles prepared according to Example 1(a) above with a modified release coating solution as detailed in Table 2. The immediate release particles are coated to varying levels up to approximately to 30% weight gain using, for example, a fluid bed appratus.

(c) Dissolution testing pH independent coated components ((i) to (v) Table 2) are tested in vitro in USP Type 1 apparatus (100 rpm) according to the following protocol: the sample is placed im 0.01 N HCl (900 ml), pH 2.0, 37° C. for all of the sampling time points.

pH dependent coated components ((vi) to (viii) Table 2) are tested in USP Type 1 apparatus (100 rpm) according to a modified version of the United States Pharmacopoeia method for enteric protection (U.S. Pat. No. 23,1995, p.1795): the sample is placed for 2 hours in 0.01 N HCl and then transferred to phosphate buffer pH 6.8 for the remainder of the sampling time points.

IR components were formulated using three different sizes of non-pareil seeds having diameter dimensions of 0.5–0.6, 0.6–0.71 and 0.71–0.85 mm, respectively. The IR particles formed by coating 0.5–0.6, 0.6–0.71 and 0.71–0.85 mm nonpareil seeds were found to release 100% of the active ingredient within 20 minutes in aqueous media.

Dissolution data for the modified release components prepared according to Example 1(b) above are shown in Tables 3 (a) to 3 (c). This data shows that release characteristics of the modified release component can be varied by changing the composition and thickness of the coating applied.

TABLE 3

(a): Dissolution data for modified release components formulated with coating solutions given in Table 2

| | Coating formulation | | | | | | | |
|---|---|---|---|---|---|---|---|---|
| | (i) | (i) | (i) | (ii) | (ii) | (ii) | (iii) | (iii) |
| | Coating level (% weight gain) | | | | | | | |
| | 4% | 6% | 10% | 4% | 6% | 8% | 4% | 6% |
| Time (hr) | % Active ingredient released | | | | | | | |
| 1 | 0 | 0 | 0 | 8.5 | 1.3 | 1.4 | 6.1 | 3.0 |
| 2 | 17.0 | 3.3 | 0 | 36.9 | 7.1 | 3.7 | 21.3 | 8.2 |
| 4 | 51.5 | 22.1 | 0 | 80.0 | 40.3 | 15.1 | 62.3 | 26.3 |
| 6 | 75.8 | 46.5 | 0 | 92.8 | 72.4 | 31.2 | 82.1 | 52.6 |
| 8 | 86.0 | 65.5 | 10.2 | 97.5 | 83.0 | 47.5 | 91.3 | 73.0 |
| 10 | 91.3 | 76.5 | 17.3 | — | — | — | 97.7 | 86.5 |

(the notation "—" indicates no measurement taken)

TABLE 2

Modified release component coating solutions

| | Amount, % (w/w) | | | | | | | |
|---|---|---|---|---|---|---|---|---|
| Ingredient | (i) | (ii) | (iii) | (iv) | (v) | (vi) | (vii) | (viii) |
| Eudragit ® RS 12.5 | 49.7 | 42.0 | 47.1 | 53.2 | 40.6 | — | — | 25.0 |
| Eudragit ® S 12.5 | — | — | — | — | — | 54.35 | 46.5 | — |
| Eudragit ® L 12.5 | — | — | — | — | — | — | — | 25.0 |
| Polyvinylpyrrolidone | — | — | — | 0.35 | 0.3 | — | — | — |
| Diethylphthalate | 0.5 | 0.5 | 0.6 | 1.35 | 0.6 | 1.3 | 1.1 | — |
| Triethylcitrate | — | — | — | — | — | — | — | 1.25 |
| Isopropyl alcohol | 39.8 | 33.1 | 37.2 | 45.1 | 33.8 | 44.35 | 49.6 | 46.5 |
| Acetone | 10.0 | 8.3 | 9.3 | — | 8.4 | — | — | — |
| Talc[1] | — | 16.0 | 5.9 | — | 16.3 | — | 2.8 | 2.25 |

[1]Talc is simultaneously applied during coating for formulations in column (i), (iv) and (vi).

TABLE 3

(b): Dissolution data for modified release components formulated with coating solutions given in Table 2

| | Coating formulation | | | | |
|---|---|---|---|---|---|
| | (iv) | (iv) | (iv) | (v) | (v) |
| | Coating level (% weight gain) | | | | |
| Time (hr) | 10% | 15% | 20% | 10% | 12.5% |
| | % Active ingredient released | | | | |
| 1 | 3.5 | 0.9 | 1.1 | 1.3 | 1.0 |
| 2 | 13.4 | 5.4 | 2.9 | 6.1 | 2.9 |
| 4 | 47.1 | 22.5 | 13.8 | 42.4 | 21.2 |
| 6 | 80.0 | 52.0 | 36.9 | 77.5 | 54.4 |
| 8 | 94.8 | 70.3 | 61.0 | 92.4 | 79.7 |
| 10 | 103 | 81.5 | 76.1 | — | — |

(the notation "—" indicates no measurement taken)

TABLE 3

(c): Dissolution data for modified release components formulated with coating solutions given in Table 2

| | Coating formulation | | | | | | | |
|---|---|---|---|---|---|---|---|---|
| | (vi) | (vi) | (vi) | (vi)* | (vii) | (vii) | (viii) | (viii) |
| | Coating level (% weight gain) | | | | | | | |
| Time (hr) | 5% | 10% | 15% | 15% | 15% | 20% | 20% | 30% |
| | % Active ingredient released | | | | | | | |
| 1 | 33.2 | 0.4 | 0 | 0 | 3.9 | 0.6 | 3.8 | 2.1 |
| 2 | 80.6 | 9.8 | 0 | 0.5 | 52.0 | 12.4 | 7.4 | 3.1 |
| 4 | 92.2 | 43.5 | 10.1 | 44.0 | 85.0 | 61.6 | 43.7 | 8.9 |
| 6 | 93.9 | 61.6 | 29.9 | 80.2 | 89.9 | 75.3 | 72.4 | 36.9 |
| 8 | 94.3 | 67.5 | 48.4 | 69.0 | 91.4 | 79.6 | 79.2 | 63.9 |
| 10 | 94.4 | — | 60.0 | — | — | — | 79.5 | 73.4 |

(the notation "—" indicates no measurement taken; "*" indicates pH of phosphate buffer was 7.4 instead of 6.8)

(d) Encapsulation of immediate and delayed release particles.

The immediate and delayed release particles prepared according to Example 1(a) and (b) above are encapsulated in size 2 hard gelatin capsules to an overall 20 mg dosage strength using, for example, a Bosch GKF 4000S encapsulation apparatus. The overall dosage strength of 20 mg methylphenidate was made up of 10 mg from the immediate release component and 10 mg from the modified release component.

Table 4 shows the dissolution profiles for two multiparticulate modified release compositions prepared using the immediate release coating solution given in Table 1 (ii) and the modified release coating solutions given in Table 2 (vii) and (viii). These results indicate that approximately 50% of the methylphenidate HCl active ingredient was released within the first half hour with release from the modified release component being delayed for about four hours.

TABLE 4

Dissolution data for compositions containing an IR component and a modified release component.

| MR coating formulation Coating level (% weight increase) Time (hr) | (vii) 30% | (viii) 30% |
|---|---|---|
| | % Active ingredient released | |
| 0 | 0 | 0 |
| 0.5 | 49.7 | 50.2 |
| 1 | 49.7 | 50.5 |
| 2 | 49.8 | 51.1 |
| 4 | 56.1 | 54.1 |
| 6 | 65.2 | 68.0 |
| 8 | 72.2 | 81.8 |
| 10 | 76.6 | 87.0 |

The dissolution profiles shown in Table 4 indicate that the compositions containing the pH dependent coated components release the methylphenidate active ingredient in a pulsed manner. A first pulse occurs before 1 hour followed by a plateau region where the release of further amounts of the active ingredient is suppressed. The plateau region is in turn followed by a second pulse of active ingredient release as indicated by the increase in drug concentration from 4 hours onward.

EXAMPLE 2

Multiparticuiate Modified Eelease Composition Containing Methylphenidate

Multiparticulate modified release methylphenidate compositions according to the present invention having an immediate release component and a modified release component having a modified release matrix material are prepared according to the formulations shown in Table 5 (a) and (b).

TABLE 5 (a)

100 mg of IR component is encapsulated with 100 mg of modified release (MR) component to give a 20 mg dosage strength product

| IR component | % (w/w) | MR component | % (w/w) |
|---|---|---|---|
| Methylphenidate HCl | 10 | Methylphenidate HCl | 10 |
| Microcrytalline cellulose | 40 | Microcrytalline cellulose | 40 |
| Lactose | 45 | Eudragit ® RS | 45 |
| Povidone | 5 | Povidone | 5 |

TABLE 5 (1)

50 mg of IR component is encapsulated with 50 mg of modified release (MR) component to give a 20 mg dosage strength product.

| IR component | % (w/w) | MR component | % (w/w) |
|---|---|---|---|
| Methylphenidate HCl | 20 | Methylphenidate HCl | 20 |
| Microcrytalline cellulose | 50 | Microcrytalline cellulose | 50 |
| Lactose | 28 | Eudragit ®RS | 28 |
| Povidone | 2 | Povidone | 2 |

(e) In vivo release

In a human cross-over biostudy, fasted healthy volunteers were dosed with 20 mg methylphenidate HCl compositions according to the present invention to compare the bioavailability of methylphenidate HCl in these compositions relative to Ritalin® (Novartis; 10 mg dosed twice at a four hour interval). Pharmacokinetic assessment was based on the plasma levels of methylphenidate measured by blood sampling at regular intervals up to 48 hours after administration. Blood samples were also taken for pre- and post-study screening.

Referring now to FIG. 1, the plasma profiles labelled "A" (modified component comprises IR particles coated with coating Table 2 (viii) at 30%) and "B" (modified component comprises IR particles coated with coating Table 2 (vii) at 30%) correspond to the plasma concentrations of methylphenidate observed in human volunteers after oral administration of the multiparticulate modified release compositions prepared according to Example 1. In both cases the plasma profile is qualitatively similar to the control, typical of prior art treatments (labelled "Control" in FIG. 1), which consists of two doses of Ritalin® IR given sequentially, four hours apart.

For the multiparticulate modified release composition according to the present invention prepared according to Example 1 above, the first peak in the plasma profile associated with the inmnediate release component is similar in terms of $c_{max}$ and peak width to the peak associated with the first dose of Ritalin® in the control profile. Profile A shows that the trough characteristic of the conventional twice daily administration (as exemplified by the control profile) is mimicked by the composition prepared according to the invention. Profile B also shows a significant fall off after the initial peak in plasma concentration. For both multiparticulate modified release compositions, the effect of the modified release component is to increase plasma concentrations four hours after administration resulting in a second peak level. This observed effect again mimics the control.

From FIG. 1 it is clear that the multiparticulate modified release compositions prepared according to the present invention mimic a typical twice daily treatment (represented by the control) in terms of the plasma profile achieved upon administration. This in vivo release of methylphenidate from compositions according to the invention was achieved without any loss in bioavailability compared to Ritalin® dosed twice daily.

In a separate study, 34 children with ADHD were dosed with 20 mg methylphenidate HCl compositions according to the present invention. A simulated classroom design was used to compare formulations "A" and "B" (corresponding to the "A" and "B," formulations described above) with placebo. Pharmacodynamic assessments were conducted over a 9 hour time period which measured both attention and deportment as measured on the SKAMP scale and functional outcome as measured by the number of math problems attempted and the number of correct answers. Each formulation demonstrated a statistical difference from placebo on all efficacy measurements. The individual efficacy evaluations showed that the "A" and "B" formulations proved to be similar with regard to deportment. With regard to attention and functional outcome, the children on the "A" formulation appeared to focus more on the tasks at hand and attempted more math problems more quickly between 4 and 6 hours than the children taking the "B" formulation.

The present invention is not to be limited in scope by the specific embodiments described herein. Various modifications of the invention in addition to those described herein will become apparent to those skilled in the art from the foregoing descnrption and the following claims.

What is claimed is:

1. A multiparticulate modified release composition containing at least one active ingredient and having a first component comprising a first population of active ingredient-containing particles and at least one subsequent component, each subsequent component comprising a subsequent population of active ingredient-containing particles, the active ingredient contained in the first and subsequent components being the same or different; wherein the at least one subsequent population of active ingredient containing particles further comprises a modified release coating or, alternatively or additionally, a modified release matrix material, such that the composition following oral delivery to a subject delivers the active ingredient or active ingredients in a pulsatile manner.

2. The multiparticulate modified release composition according to claim 1, wherein the composition comprises a first component and one subsequent component.

3. The multiparticulate modified release composition according to claim 2, wherein the first component comprises an immediate release component and the subsequent component is a modified release component.

4. The multipaiticulate modified release composition according to claim 3, wherein the modified release component comprises particles having a modified release coating.

5. The multiparticulate modified release composition according to claim 3, wherein the modified release component comprises a modified release matrix material.

6. The multiparticulate modified release composition according to claim 1, wherein the first population of active ingredient-contaning particles and the at least one subsequent population of active ingredient-containing particles comprise the same active ingredient.

7. The multiparticulate modified release composition according to claim 1, wherein the first population of active ingredient-containing particles contains two or more active ingredients.

8. The multiparticulate modified release composition according to claim 1, wherein the at least one subsequent population of active ingredient-containing particles contains two or more active ingredients.

9. The multiparticulate modified release composition according to claim 1, wherein the active ingredient comprises substantially one optically pure enantiomer or a mixture, racemic or otherwise, of enantiomers.

10. The multiparticulate modified release composition according to claim 1, wherein at least one of the first and subsequent components further comprise an enhancer.

11. The multiparticulate modified release composition according to claim 1, wherein the amount of active ingredient contained in the first and subsequent components is the same or different.

12. The multiparticulate modified release composition according to claim 11, wherein the amount of active ingredient contained in each component is from about 0.1 mg to about 1 g.

13. The multiparticulate modified release composition according to claim 6, wherein the active ingredient is methylphenidate or a pharmaceutically acceptable salt thereof, an enantiomer or mixtures thereof or mixtures thereof.

14. The multipatticulate modified release composition according to claim 1, wherein the first and subsequent populations of active ingredient-containing particles have different in vitro dissolution profiles.

15. The multiparticulate modified release composition according to claim 1, wherein the first component is an immediate release component and the at least one subsequent component is a modified release component.

16. The multiparticulate modified release composition according to claim 15, which in operation releases substantially all of the active ingredient from the first population of active ingredient-containing particles prior to release of the active ingredient from the subsequent population of active ingredient-containing particles.

17. The multiparticulate modified release composition according to claim 1, wherein the in vivo release of the active ingredient in the subject mimics the in vivo release of the same active ingredient administered in the form of two or more doses of immediate release forms of the active ingredient.

18. The multiparticulate modified release composition according to claim 13, wherein the in vivo release of the active ingredient in the subject mimics the in vivo release of the same active ingredient administered in the form of two or more doses of immediate release forms of the active ingredient.

19. The multiparticulate modified release composition according to claim 16, wherein the mean in vitro dissolution profile in an aqueous medium is such that about 50 to 100% of the active ingredient contained in the first population of active ingredient containing particles is released within four hours, and about 25 to 55% of the active ingredient contained in the subsequent population of active ingredient containing particles is released between four and eight hours.

20. The multiparticulate modified release composition according to claim 19, wherein the mean in vitro dissolution profile in an aqueous medium is such that about 80 to 100% of the active ingredient contained in the first population of active ingredient containing particles is released within four hours, and about 28 to 55% of the active ingredient contained in the subsequent population of active ingredient containing particles is released between four and eight hours.

21. A solid oral dosage form comprising a multiparticulate modified release composition according to claim 1.

22. The solid oral dosage form according to claim 21 comprising a blend of first and subsequent active ingredient-containing particles filled into hard gelatin or soft gelatin capsules.

23. The solid oral dosage form according to claim 21, wherein the first and subsequent components are separately and independently compressed into mini-tablets and filled into hard or soft gelatin capsules.

24. The solid oral dosage form according to claim 21, wherein the first component is compressed into the first layer of a multilayer tablet and the at least one subsequent component is compressed into a subsequent layer of the multilayer tablet.

25. The solid oral dosage form according to claim 21, wherein the first and subsequent components are incorporated in a rapidly dissolving dosage form.

26. The solid oral dosage form according to claim 25, wherein the rapidly dissolving dosage form is a fast-melt tablet dosage form.

27. A method, wherein a multiparticulate modified release composition comprising:
   a. a first population of active ingredient containing particles and
   b. at least one subsequent population of active ingredient containing particles, wherein the subsequent population of active ingredient containing particles further comprises a coating selected from the group consisting of a modified release coating and a modified release matrix material, and wherein oral administration of the composition to a subject in need of the active ingredient releases the active ingredient in a pulsatile manner.

28. The method of claim 27, wherein the in vitro dissolution profile of the multiparticulate modified release composition in an aqueous medium is such that about 50% of the total active ingredient is released within about 30 minutes, about 4% of the total active ingredient is released between about 30 minutes and 4 hours, and about 28% of the active ingredient is released between about four hours and eight hours.

29. The method of claim 27, wherein the active ingredient is an active ingredient for the treatment of attention deficit disorder.

30. A method of treatment of a condition which is characterised by the build up of patient tolerance to an active ingredient administered in the treatment of the condition comprising administering a therapeutically effective amount of a multiparticulate modified release composition according to claim 1.

31. A method of treatment of attention deficit disorder comprising administering a therapeutically effective amount of a multiparticulate modified release composition according to claim 1.

32. A method of treatment of attention deficit disorder comprising administering a therapeutically effective amount of a multiparticulate modified release composition according to claim 13.

33. The composition according to claim 3, wherein the modified release component comprises a pH dependent polymer coating that releases a pulse of active ingredient from the modified release component following a delay time.

34. The composition according to claim 33, wherein the pH dependent polymer coating comprises methacrylate copolymers.

35. The composition according to claim 33, wherein the pH dependent polymer coating comprises a mixture of methacrylate and ammonio methacrylate copolymers in a ratio sufficient to achieve a pulse of active ingredient from the modified release component following a delay time.

36. The composition according to claim 35, where the ratio of methacrylate to ammonio methacryiate copolymers is 1:1.

37. The method of claim 28, wherein the active ingredient is selected from the group consisting of methylphenidate, a pharmaceutically acceptable salt of methylphenidate, an enantiomer of methylphenidate and a mixture of methylphenidate, a pharmaceutically acceptable salt of methylphenidate and an enantiomer of methylphenidate.

* * * * *

UNITED STATES PATENT AND TRADEMARK OFFICE
CERTIFICATE OF CORRECTION

PATENT NO. : 6,228,398 B1
DATED : May 8, 2001
INVENTOR(S) : John G. Devane et al.

It is certified that error appears in the above-identified patent and that said Letters Patent is hereby corrected as shown below:

Title Page,
Item [75], please add inventor -- Gurvinder Singh Rekhi, Suwanee, Georgia --
Item [57], ABSTRACT,
Line 8, delete "compnsimg" and substitute -- comprising -- therefor Column 1,
Line 55, delete "rnethylphenidate" and substitute -- methylphenidate -- therefor Column 2,
Line 14, delete "give n period of tine." and substitute -- given period of time. -- therefor Column 3,
Line 30, delete "armmonio" and substitute -- ammonia -- therefor
Line 31, delete "certa" and substitute -- certain -- therefor
Line 33, delete "provice" and substitute -- provide -- therefor Column 4,
Line 54, delete "mimimising" and substitute -- minimising -- therefor Column 5,
Line 9, delete "taat" and substitute -- that -- therefor
Line 26, delete "A—20" and substitute -- A-20 -- therefor
Line 32, delete "B—20" and substitute -- B-20 -- therefor
Line 38, delete "Control-two" and substitute -- Control-two -- therefor Column 6,
Line 38, delete "hoimone" and substitute -- hormone -- therefor
Line 65, delete "or different For example," and substitute -- or different. For example, -- therefor Column 7,
Line 34, delete "frrst" and substitute -- first -- therefor Column 10,
Line 33, delete "flrher" and substitute -- further -- therefor Column 11,
Line 22, delete "nonpareil" and substitute -- non-pareil -- therefor

UNITED STATES PATENT AND TRADEMARK OFFICE
CERTIFICATE OF CORRECTION

PATENT NO.    : 6,228,398 B1
DATED         : May 8, 2001
INVENTOR(S)   : John G. Devane et al.

It is certified that error appears in the above-identified patent and that said Letters Patent is hereby corrected as shown below:

Column 12,
Line 4, delete "im" and substitute -- in -- therefor
Line 19, delete "nonpareil" and substitute -- non-pareil -- therefor Column 14,
Line 28, delete "Eelease" and substitute -- Release -- therefor
Line 50, delete "TABLE 5 (1)" and substitute -- TABLE 5 1(b) -- therefor Column 15,
Line 63, delete "descnrption" and substitute -- description -- therefor Column 16,
Line 19, delete "multipaiticulate" and substitute -- multiparticulate -- therefor
Line 58, delete "multipatticulate" and substitute -- multiparticulate -- therefor Column 18,
Line 46, delete "ammonio" and substitute -- ammonia -- therefor
Line 50, delete "ammonio" and substitute -- ammonia -- therefor Signed and Sealed this Twenty-fifth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,228,398 B1
DATED : May 8, 2001
INVENTOR(S) : Devane et al.

It is certified that error appears in the above-identified patent and that said Letters Patent is hereby corrected as shown below:

Column 16,
Line 27, delete "ingredient-containg" and insert -- ingredient-containing --; and Column 18,
Line 50, delete "methacryiate" and insert -- methacrylate --.

Signed and Sealed this

Sixth Day of June, 2006

JON W. DUDAS
*Director of the United States Patent and Trademark Office*